United States Patent [19]

Driver

[11] Patent Number: 4,540,688

[45] Date of Patent: Sep. 10, 1985

[54] β-LACTAM ANTIBIOTICS

[75] Inventor: Michael J. Driver, Horsham, England

[73] Assignee: Beecham Group p.l.c., England

[21] Appl. No.: 489,183

[22] Filed: Apr. 27, 1983

[30] Foreign Application Priority Data

Apr. 29, 1982 [GB] United Kingdom ................ 8212525

[51] Int. Cl.$^3$ .................. A61K 31/43; A61K 31/495; C07D 499/54
[52] U.S. Cl. ................................ 514/196; 260/239.1; 514/197
[58] Field of Search ..................... 260/239.1; 424/250, 424/271

[56] References Cited

U.S. PATENT DOCUMENTS

| | | | |
|---|---|---|---|
| 3,487,074 | 12/1969 | Sheehan | 260/239.1 |
| 4,189,482 | 2/1980 | Truener et al. | 424/250 |
| 4,229,348 | 10/1980 | Oi et al. | 260/239.1 |
| 4,349,551 | 9/1982 | Bentley et al. | 424/250 |
| 4,416,883 | 11/1983 | Bentley | 424/250 |

FOREIGN PATENT DOCUMENTS 0006532 1/1980 European Pat. Off. .
2043627 10/1979 United Kingdom .

Primary Examiner—Natalie Trousof
Assistant Examiner—Vera C. Clarke
Attorney, Agent, or Firm—Jacobs & Jacobs

[57] ABSTRACT

Compounds of formula (I) or a pharmaceutically acceptable salt or in vivo hydrolysable ester thereof have antibacterial activity:

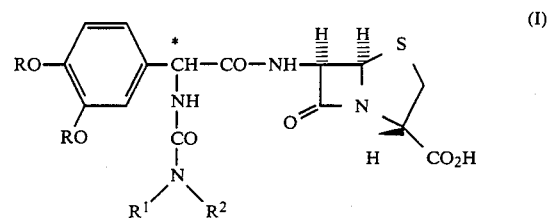

wherein R is hydrogen, $C_{1-6}$ alkylcarbonyl or $C_{1-6}$ alkyl; $R^1$ is hydrogen or hydrocarbon; $R^2$ is hydrogen, or optionally substituted hydrocarbon or optionally substituted heterocyclyl or $CXR^d$, where X is O or S and $R^d$ is hydrogen or optionally substituted hydrocarbon or optionally substituted heterocyclyl; or $R^1$ and $R^2$ together with the nitrogen to which they are attached, form an optionally substituted heterocyclyl group. A process for the preparation of such compounds and compositions comprising them, are also described.

30 Claims, No Drawings

β-LACTAM ANTIBIOTICS

This invention relates to a class of penicillin derivatives which have antibacterial activity and are of value in the treatment of infections in animals, especially mammals, including man, caused by a wide range of organisms. In particular, the invention relates to a class of bis nor penicillin derivatives. The invention also relates to a process for the preparation of such compounds and to pharmaceutical compositions comprising them.

According to the present invention there is provided a compound of formula (I) or a pharmaceutically acceptable salt or in vivo hydrolysable ester thereof:

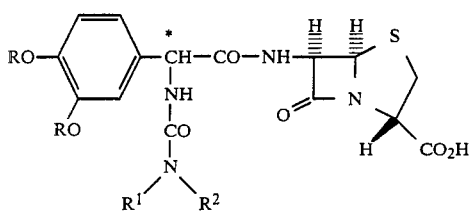

wherein R is hydrogen, $C_{1-6}$ alkylcarbonyl or $C_{1-6}$ alkyl; $R^1$ is hydrogen or hydrocarbon; $R^2$ is hydrogen, or optionally substituted hydrocarbon or optionally substituted heterocyclyl or $CXR^d$, where X is 0 or S and $R^d$ is hydrogen or optionally substituted hydrocarbon or optionally substituted heterocyclyl; or $R^1$ and $R^2$ together with the nitrogen to which they are attached, form an optionally substituted heterocyclyl group.

Preferably R is hydrogen or acetyl.
In particular R is hydrogen.
Preferably $R^1$ is hydrogen or $C_{1-6}$ alkyl.

Suitable alkyl groups include straight and branched chain alkyl groups containing from 1 to 6 carbon atoms, such as methyl, ethyl, propyl and butyl. A particular alkyl group is methyl.

Preferably $R^2$ is a group, $COR^d$, or $R^1$ and $R^2$ together with the nitrogen atom to which they are attached form an optionally substituted five- or six-membered heterocyclic group containing one or two nitrogen atoms.

Preferably $R^d$ is hydrogen or an optionally substituted aryl group.

More preferably $R^d$ is an aryl group optionally substituted with up to three groups selected from halogen, $C_{1-6}$ alkyl, $C_{1-6}$ alkoxy, hydroxy, amino, nitro, carboxy, $C_{1-6}$ alkoxycarbonyl, $C_{1-6}$ alkylcarbonyl or $C_{1-6}$ alkylcarbonyloxy. Particular substituents include halogen, and $C_{1-6}$ alkylcarbonyloxy.

Examples of suitable pharmaceutically acceptable in vivo hydrolysable ester groups include those which break down readily in the human body to leave the parent acid or its salts or the parent hydroxyl groups. Those esters which break down to give the parent acid include, for example acyloxyalkyl groups, such as acetoxymethyl, pivaloyloxymethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups, such as dimethylaminomethyl, dimethylaminoethyl, diethylaminomethyl or diethylaminoethyl; and lactone groups such as phthalidyl or dimethoxyphthalidyl.

The compounds of the present invention contain both an amino group and a carboxyl group and may, therefore, exist as the zwitterion or may form salts with suitable acids or bases.

Suitable pharmaceutically acceptable salts of the compounds of formula (I) include metal salts, e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabrietylamine, N,N'-bisdehydroabietylamine, ethylenediamine, or bases of the pyridine type such as pyridine, collidine or quinoline.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)-alkyl, aryl, and aryl($C_{1-6}$)alkyl.

The term 'heterocyclyl' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$) alkyl, aryl or oxo groups.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl $C_{1-6}$ alkylcarbonyloxy, or $C_{1-6}$ alkylcarbonyl groups.

Suitable optional substituents for the hydro-carbon, heterocyclic groups and organic radicals include $C_{1-6}$ alkyl, heterocyclic, amino, $C_{1-6}$ alkanoyl-amino, mono, di- and tri- ($C_{1-6}$) alkylamino, hydroxy, $C_{1-6}$ alkoxy, mercapto, $C_{1-6}$ alkylthio, heterocyclyl-thio, arylthio, sulphamoyl, carbamoyl, amidino, guanidino, nitro, chloro, bromo, fluoro, carboxy and salts and esters thereof, $C_{1-6}$ alkanoyloxy, aryl-carbonyl and heterocyclylcarbonyl.

The carbon atom marked * in formula (I) is asymmetric and the compound may be derived from the side-chain having a D, L or DL configuration at that position. All forms of compound (I) are included in this invention. Suitably, the carbon atom marked * is derived from the D-configuration and is conveniently referred to as the D-bis nor penicillin.

Suitable substituents for the five- or six-membered heterocyclic group include the alkyl, alkenyl, alkynyl, cycloalkyl or cycloalkenyl group, optionally substituted phenyl, oxo, the hydroxy group optionally substituted by alkyl, alkenyl, cycloalkyl, phenyl, pyridyl, pyrimidyl or benzyl, the optionally substituted mercapto group, the alkylsulphenyl group, or the amino group optionally substituted by an alkyl, alkenyl, cycloalkyl, phenyl, substituted phenyl or benzyl group. Alternatively two substituents on the ring may form the residue of a further carbocyclic or heterocyclic ring.

One preferred sub-group within the present invention provides a compound of formula (II) or a pharmaceutically acceptable salt or in vivo hydrolysable ester thereof:

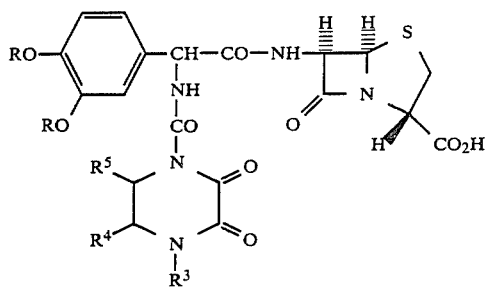

wherein R is as defined hereinbefore, R³ represents hydrogen or C₁₋₆ alkyl; R⁴ and R⁵ are the same or different and represent hydrogen, C₁₋₆ alkyl, halogen, amino, hydroxy or C₁₋₆ alkoxy.

Suitable C₁₋₆ alkyl groups for the groups R³, R⁴ and R⁵ include methyl, ethyl, n- and iso-propyl, n-, sec-, iso- and tert-butyl. Preferably R³ is ethyl. Preferably R⁴ and R⁵ are hydrogen.

Specific compounds within this invention include the following:

6,β[D-2-(4-ethyl-2,3-dioxopiperazine-1-carbonylamino)-2-(3,4-dihydroxyphenyl)]acetamidobisnorpenicillanic acid;

6,β-[DL-2-(4-ethyl-2,3-dioxopiperazine-1-carbonylamino)-2-(3,4-dihydroxyphenyl)]acetamidobisnorpenicillanic acid;

6,β-[D,L-2-[3-(3,4-diacetoxyphenylcarbonyl)-3-methyl-1-ureido]-2-(3,4-diacetoxyphenyl)]acetamidobisnorpenicillanic acid;

6,β-[D,L-2-(3-phenylcarbonyl-3-methyl-1-ureido)-2-(3,4-dihydroxyphenyl)]acetamidobisnorpenicillanic acid;

6,β-[D-2-[3-(4-chlorophenylcarbonyl)-3-methyl-1-ureido]-2-(3,4-dihydroxyphenyl)]acetamidobisnorpenicillanic acid.

The compounds of formula (I) may be prepared by reacting a compound of formula (III):

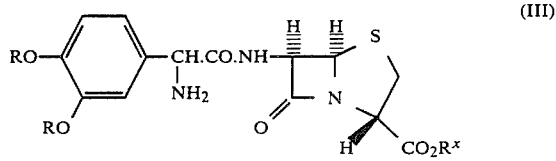

wherein R is as hereinbefore defined, the α-amino group is optionally substituted with a group which permits acylation to take place, and R$^x$ is hydrogen or a carboxyl-blocking group, with an N-acylating derivative of an acid of formula (IV):

wherein R¹ and R² are as defined with respect to formula (I) above and any reactive groups may be protected; and thereafter, if necessary, carrying out one or more of the following steps:

(i) removing any carboxyl-blocking group R$^x$;
(ii) removing any protecting groups on the side-chain group;
(iii) converting the product into a salt or in vivo hydrolysable ester thereof.

Suitable groups which permit acylation to take place and which are optionally present on the amino group of the starting material of the formula (III) include N-silyl, N-stannyl and N-phosphorus groups, for example trialkylsilyl groups such as trimethylsilyl, trialkyltin groups such as tri-n-butyltin, groups of formula —P.R$^a$R$^b$ wherein R$^a$ is an alkyl, haloalkyl, aryl, aralkyl, alkoxy, haloalkyl, aryl, haloalkoxy, aryloxy, aralkyloxy or dialkylamino group, R$^b$ is the same as R$^a$ or is halogen or R$^a$ and R$^b$ together form a ring; suitable such phosphorus groups being —P(OC₂H₅)₂, —P(C₂H₅)₂, and

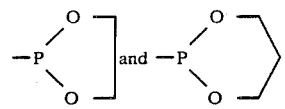

Suitable carboxyl-blocking derivatives for the group —CO₂R$^x$ in formula (III) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with tri-lower-alkylamines; N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for R$^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula —N=CHR$^o$ where R$^o$ is aryl or heterocyclic, or an in vivo hydrolysable ester radical such as defined above.

The carboxyl group may be regenerated from any of the above esters by usual methods appropriate to the particular R$^x$ group, for example, acid- and base-catalysed hydrolysis, or by enzymically-catalysed hydrolysis, or by hydrogenation.

A reactive N-acylating derivative of the acid (III) is employed in the above process. The choice of reactive derivative will, of course, be influenced by the chemical nature of the substituents of the acid.

Suitable N-acylating derivatives include an acid halide, preferably the acid chloride or bromide. Acylation with an acid halide may be affected in the presence of an acid binding agent for example, tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C₁₋₆)-1,2,alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as aqueous acetone, aqueous tetrahydrofuran, ethyl acetate, dimethylacetamide, dimethylformamide, acetonitrile, dichloromethane, 1,2- dichloroethane, or mixtures thereof. Alternatively, the reaction may be carried out in an unstable emulsion of water-immiscible solvent, especially an aliphatic ester or ketone, such as methyl isobutyl ketone or butyl acetate.

Alternatively, the N-acylating derivative of the acid (IV) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (IV) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol or 8-hydroxyquinoline; or amides such as N-acylsaccharins or N-acylphthalimides; or an alkylidene iminoester prepared by reaction of the acid (IV) with an oxime.

Other reactive N-acylating derivatives of the acid (IV) include the reactive intermediate formed by reaction in situ with a condensing agent such as a carbodiimide, for example N,N-diethyl-, dipropyl- or diisopropylcarbodiimide, N,N'-dicyclohexylcarbodiimide or N-ethyl-N'-dimethylaminopropylcarbodiimide; a suitable carbonyl compound, for example N,N'-carbonyldiimidazole or N,N'-carbonylditriazole; an isoxasolinium salt, for example N-ethyl-5-phenylisoxazolinium-2-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3$-$C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

The compounds of formula (I) may also be prepared by reacting a compound of formula (V):

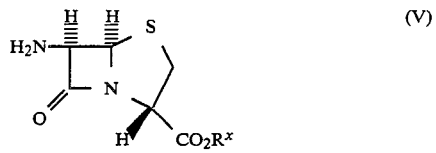

wherein the amino group is optionally substituted with a group which permits acylation to take place and $R^x$ is as defined with respect to formula (III) above, with an N-acylating derivative of an acid of formula (VI):

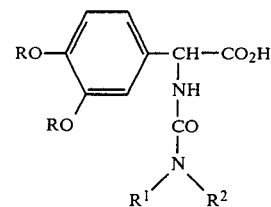

wherein R, $R^1$ and $R^2$ are as defined with respect to formula (I) and any reactive groups therein may be protected; and thereafter, if necessary, carrying out one or more of the following steps:

(i) removing any carboxyl-blocking group $R^x$;

(ii) removing any protecting groups on the side-chain group;

(iii) converting the product into a salt or in vivo hydrolysable ester thereof.

The intermediate compound of formula (III) may be prepared by reacting a compound of formula (V) as hereinbefore defined, with an N-acylating derivative of an acid of formula (VI)

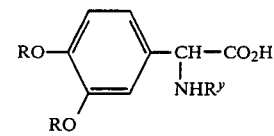

wherein R is as defined with respect to formula (I) and any reactive groups therein may be protected and $R^y$ is an amino-protecting group; and thereafter removing protecting group $R^y$.

Suitable N-acylating derivatives, carboxyl protecting groups and reaction conditions include those described hereinbefore.

Suitable amino-protecting groups $R^y$ are those well-known in the art which may be removed under conventional conditions without disruption of the remainder of the molecule.

The starting material of formula (V) is disclosed in British Pat. No. 1,546,622.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for administration may be in unit dose presentation form, and may contain conventional excipients such as binding agents, for example syrup, acacia, gelatin, sorbitol, tragacanth, or polyvinylpyrollidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parental suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the composition comprise dosage units, each unit will preferably contain from 50–500 mg of the active ingredient. The dosage as employed for adult human treatment will preferably range from 100 to 300 mg per day, for instance 1500 mg per day depending on the route and frequency of administration.

The compound of formula (I) may be the sole therapeutic agent in the compositions of the invention or a combination with other antibiotics or with a β-lactamase inhibitor may be employed.

Advantageously, the compositions also comprise a compound of formula (VIII) or a pharmaceutically acceptable salt or ester thereof:

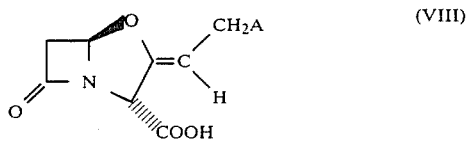

(VIII)

wherein A is hydroxyl, substituted hydroxyl, thiol, substituted thiol, amino, mono- or di-hydrocarbyl-substituted amino, or mono- or di-acylamino.

A further advantageous composition comprises a compound of formula (I) or a pharamceutically acceptable salt or in vivo hydrolysable ester thereof together with a compound of formula (IX) or a pharmaceutically acceptable salt or in vivo hydrolysable ester thereof:

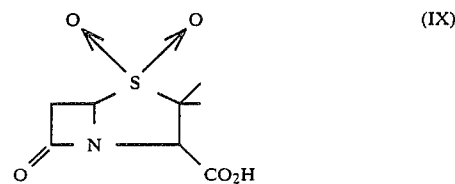

(IX)

The following Examples illustrate the preparation of the compounds of this invention.

EXAMPLE 1

Sodium 6,β-[D-2-(4-ethyl-2,3-dioxopiperazine-1-carbonylamino)-2-(3,4-dihydroxyphenyl)]acetamidobisnorpenicillanate (a)

D-2(4-Ethyl-2,3-dioxopiperazine-1-carbonylamino)-2-(3,4-dihydroxyphenyl)acetic acid D-3,4-Dihydroxyphenyl glycine (2.5 g, 13.7 mmol) in trimethylsilyldiethylamine (15 ml) under nitrogen was heated under reflux for 0.3 h. The solution was evaporated to dryness and the residue dissolved in dry dichloromethane (20 ml), cooled to 0° C. and then treated with a solution of 4-ethyl-2,3-dioxopiperazine-1-carbonylchloride (2.7 g, 13.7 mmol) in dichloromethane (10 ml). The mixture was allowed to warm to 21° C., stirred for 1 h, poured into water (50 ml) and stirred for a further 0.2 h. The aqueous phase was basified to pH 7.5 and the organic phase then separated and discarded. Acidification of the aqueous solution to pH 1.5 with dilute hydrochloric acid followed by extraction with 10% n-butanol in ethyl acetate (3×50 ml), drying of the combined extracts (MgSO$_4$) and evaporation gave an off-white foam. This product dissolved in acetone (10 ml) was dropped into diethyl ether (100 ml) with vigorous stirring to give the title compound as a solid (1.3 g, 27%) m.p. softens above 115° C. melts 140°–145° C. (dec), $v_{max}$ (Nujol) 3300 (br), 1710, 1675, 1520 cm$^{-1}$ δ(d$^6$-acetone 9.8 (1H, d, J 7 Hz, NH), 6.9 (3H, m, aryl protons), 5.4 (4H, m, reduces to 1H, s, C$\underline{H}$CO$_2$H, on the additon D$_2$O), 4.2–3.3 (6H, m, C$\underline{H}_2$-C$\underline{H}_2$, C$\underline{H}_2$CH$_3$) and 1.2 (3H, t, J 7 Hz, CH$_2$C$\underline{H}_3$) ppm.

(b)

D-2-(4-Ethyl-2,3-dioxopiperazine-1-carbonylamino)-2-(3,4-diacetoxyphenyl)acetic acid D-2(4-Ethyl-2,3-dioxopiperazine-1-carbonylamino)-2-(3,4-dihydroxyphenyl) acetic acid (0.7 g, 2 mmol) in dry tetrahydrofuran (10 ml) under N$_2$ was cooled to 0° C. when pyridine (0.48 ml, 6 mmol) and acetic anhydride (0.47 ml, 5 mmol) were added. The solution was allowed to warm to 21° C. and stirred for 1.5 h. The tetrahydrofuran was then evaporated in vacuo and the residue partitioned between ethyl acetate and water at pH 1.5. The organic phase was separated, washed with brine, dried (MgSO$_4$) and evaporated to give a foam.

This crude material was dissolved in dichloromethane (10 ml) and dropped into diethyl ether (100 ml) with vigorous stirring to give a solid which was filtered, washed with ether and dried (0.66 g, 77%) $\nu_{max}$ (Nujol) 1780, 1710, 1675 cm$^{-1}$ δ(CD$_3$OD/d$^6$-acetone) 10.1 (1H, d, J 7 Hz, NH ), 7.5–7.0 (3H, m, aryl protons), 5.4 (1H, d, J 7 Hz, CH), 4.2–3.2 (6H, m, CH$_2$CH$_2$, CH$_2$CH$_3$), 2.2 (6H, s, OCOCH$_3$×2) and 1.1 (3H, t, J 7 Hz, CH$_2$CH$_3$) ppm.

(c) Benzyl 6β-[D,2(4-ethyl-2,3-dioxopiperazine-1-carbonylamino)-2-(3,4-diacetoxyphenyl)]acetamido bisnorpenicillanate Benzyl 6,β-aminobisnorpenicillanate (0.28 g, 1 mmol) in dry dichloromethane (10 ml) with dicyclohexylcarbodiimide (0.21 g, 1 mmol) at 0° C. was treated with D-2(4-ethyl-2,3-dioxopiperazine-1-carboxylamino)-2-(3,4-diacetoxyphenyl)acetic acid (0.43 g, 1 mmol) in dry dichloromethane (10 ml). The mixture was allowed to warm to 21° C. and stirred for 2.5 h when precipitated urea was removed by filtration. The filtrate was washed with dilute hydrochloric acid, dilute sodium bicarbonate, brine then dried (MgSO$_4$) and evaporated to give a yellow foam. This crude material was columned on silica eluting with ethyl acetate to give the product as a foam (0.32 g, 46%) $\nu_{max}$ (DCM) 1790, 1775, 1740, 1720, 1690, 1500, 1215 and 1190 cm$^{-1}$; δ(CDCl$_3$/d$_6$ acetone) 10.0 (1H, d, J 7 Hz, NH), 8.1 (1H, d, J 8 Hz, NH), 7.4–7.0 (8H, aryl protons), 5.7–4.9 (6H, H-6, H-5, H-3, -H, CH$_2$), 4.2–3.3 (8H, m, CH$_2$-CH$_2$, CH$_2$-CH$_3$, H-2×2), 2.2 (6H, s, OCOCH$_3$×2) and 1.2 (3H, t, J 7 Hz, CH$_2$CH$_3$) ppm.

(d) Sodium 6,β-[D,2(4-ethyl-2,3-dioxopiperazine-1-carbonylamino)-2-(3,4-diacetoxyphenyl)]acetamido bisnorpenicillanate Benzyl 6,β-[D-2(4-ethyl-2,3-dioxopiperazine-1-carbonylamino)-2-(3,4-diacetoxyphenyl)]acetamido bisnorpenicillanate (0.18 g, 0.26 mmol) in tetrahydrofuran (10 ml) and water (4 ml) was hydrogenated for one hour in the presence of 10% palladium on charcoal (0.2 g). The mixture was filtered through celite and the filtrate evaporated to near dryness. The residue was partitioned between ethyl acetate and water at pH 6.5, the aqueous phase separated and freeze-dried to give the product as a white powder (0.1 g, 62%) $\nu_{max}$ (Nujol) 1770, 1720, 1680 and 1610 cm$^{-1}$; δ(D$_2$O) 7.49 (1H, dd, J 7 Hz and 1.5 Hz, H-5), 7.42 (1H, d, J 1.5 Hz, H-2'), 7.33 (1H, d, J 7 Hz, H-6), 5.56 (1H, s, CH), 5.42 (1H, d, J 4 Hz, H-6), 5.27 (1H, d, J 4 Hz, H-5), 4.88 (H-3 masked by solvent), 4.00 (2H, m, N-CH$_2$CH$_2$), 3.75–3.26 (6H, m, N-CH$_2$, CH$_2$CH$_3$, H-2×2), 2.33 (6H, s, OCOCH$_3$×2) and 1.19 (3H, t, J 7 Hz, CH$_2$CH$_3$) ppm.

(e) Sodium 6,β-[D-2(4-ethyl-2,3-dioxopiperazine-1-carbonylamino)-2-(3,4-dihydroxyphenyl)]acetamido bisnorpencillanate Sodium 6,β-[D-2(4-ethyl-2,3-dioxopiperazine-1-carbonylamino)-2-(3,4-diacetoxyphenyl)]acetamidobisnorpenicillanate (20 mg, 0.032 mmol) in water (10 ml) was treated with dilute sodium bicarbonate solution until the pH had risen to 7.5. The enzyme subtilisin A on a polymer support (200 mg) was added and the mixture stirred at 21° C. for 2.5 h when the mixture was filtered, the filtrate acidified to pH 1.5 and extracted with ethyl acetate (4×20 ml). The combined extracts were washed (brine), dried (MgSO$_4$) and evaporated to give the product as a colourless solid which was dissolved in water at pH 6.5 and freeze-dried to give the title compound as a white powder (8 mg, 46%) $\nu_{max}$ (Nujol) 1770, 1720, 1685 and 1615 cm$^{-1}$; δ(D$_2$O) 7.15–6.92 (3H, m, aryl protons), 5.49 (1H, s, CH), 5.35–5.28 (2H, m, H-6, H-5), 4.90 (1H, m, H-3), 4.02 (2H, m, CH$_2$CH$_2$), 3.71 (2H, m, CH$_2$CH$_2$), 3.50 (2H, q, J 7 Hz, CH$_2$CH$_3$), 3.38 (2H, m, H-2×2) and 1.19 (3H, t, J 7.5 Hz, CH$_2$CH$_3$) ppm.

EXAMPLE 2

Sodium 6,β[D,L-2(4-ethyl-2,3-dioxopiperazine-1-carbonylamino)-2-(3,4-dihydroxyphenyl)]acetamido bisnorpenicillanate The title compound was prepared employing an analogous sequence of reactions as described in Example 1 starting from DL-3,4-dihydroxyphenylglycine.

EXAMPLE 3

Sodium 6,β[D-2-(4-ethyl-2,3-dioxopiperazine-1-carbonylamino)-2-(3,4-dihydroxyphenyl)]acetamidobisnorpenicillanate (a) D-2-(4-Ethyl-2,3-dioxopiperazine-1-carbonylamino)-2-(3,4-dihydroxyphenyl) acetic acid D-3,4-Dihydroxyphenyl glycine (0.92 g, 5 mmol) in 1,1,1,3,3,3-hexamethyl-disilazane (8 ml) and trimethylsilyl chloride (2 ml) was heated, in an inert atmosphere, under reflux for 2 hours. Excess silylating agents and by products were removed by evaporation in vacuo and the residue was dissolved in dry dichloromethane (10 ml). The solution was cooled to 0° C. when 4-ethyl-2,3-dioxopiperazine-1-carbonyl chloride (10 mg, 5 mmol) in dry dichloromethane (5 ml) was added. The mixture was stirred for 1.5 hours at 21 0° C., evaporated to low bulk and the residue dissolved in 2:1 acetone/water (30 ml) at pH 1.5 with vigorous stirring. After 0.3 hours the acetone was evaporated, the residue basified to pH 7.5 with dilute sodium bicarbonate and washed with ethyl acetate. The aqueous phase was saturated with sodium chloride, layered with ethyl acetate and acidified to pH 2 with dilute hydrochloric acid. The aqueous phase was separated, extracted several times with ethyl acetate and the combined organic phases, washed with brine dried (MgSO$_4$) and evaporated to give a white solid (0.7 g, 40%). IR $\nu_{max}$ (Nujol) 3300 (b), 2950 (b), 1720, 1690 cm$^{-1}$ Pmr δ(d$^6$acetone/D$_2$O) 6.9 (3H, m, aryl protons), 5.4 (1H, s, CH), 4.3–3.4 (6H, m, CH$_2$CH$_2$, CH$_2$CH$_3$) and 1.3 (3H, t, CH$_2$CH$_3$)ppm.

(b) Sodium D-2-(4-ethyl-2,3-dioxopiperazin-1-carbonylamino)-2-(3,4-dihydroxyphenyl)acetate The acid (0.5 g, 1.4 mmol) from example 3(a) was partitioned between ethyl acetate and water at pH 6.5. The aqueous phase was separated and freeze-dried to give the sodium salt as a white amorphous solid which was dried over phosphorous pentoxide in vacuo (0.45 g, 85%).

Ir $\nu_{max}$ (Nujol) 3300 (b) 1715, 1695 and 1600 cm$^{-1}$.

(c) Benzyl 6,β-[D-2-(4-ethyl-2,3-dioxopiperazine-1-carbonylamino)-2-(3,4-dihydroxyphenyl)]acetamidobisnorpenicillanate The sodium salt (0.22 g, 0.6 mmol) from example 3(b) in dry tetrahydrofuran (10 ml) was cooled to −10° C. when N-methylmorpholine (2 drops) and then methyl chloroformate (0.045 ml, 0.6 mmol) were added. The mixture was stirred for 0.75 hours, evaporated to low bulk, diluted with dry dichloromethane (5 ml) and added to a stirred solution of benzyl 6β-aminobisnorpenicillanate (0.16 g, 0.6 mmol) in dry dichloromethane (5 ml). After 2 hours the solution was washed with dilute hydrochloric acid, dilute sodium bicarbonate solution, brine, then dried (MgSO$_4$) and evaporated to give a foam (0.23 g).

This crude material was columned rapidly on silica gel eluting with 10% methanol in ethyl acetate to give the product as a white foam (0.11 g, 31%)

Ir $\nu_{max}$(DCM) 330(b) 1795, 1745, 1715, 1690, 1185$^{-1}$ Pmr δ(CDCl$_3$) 7.35 (5H, m, aryl protons), 6.82 (3H, m, 3,4-dihydroxyphenyl protons), 5.60 (1H,d,H-6), 5.29 (1H, s, CH), 5.27 (H, d, H-5), 5.19 (2H, s, CH$_2$), 4.95 (1H, t, H-3), 4.00 (2H, m, CON-CH$_2$), 3.55 (4H, m, CH$_2$CH$_3$ CH$_2$CH$_2$), 3.35 (2H, d, H-2×2) and 1.22 (3H, t, CH$_2$CH$_3$) ppm

(d) Sodium 6,β-[D-2-(4-ethyl-2,3-dioxopiperazine-1-carbonylamino)-2-(3,4-dihydroxyphenyl)]acetamidobisnorpenicillanate.

The ester (0.1 g, 0.16 mmol) from example 3(c) in tetrahydrofuran (5 ml) with 10% palladium on charcoal (0.1 g) was hydrogenated for 0.75 h. More catalyst (0.1 g) was added and hydrogenolysis continued for a further 0.75 h. The mixture was filtered through 'Celite', evaporated and the residue partitioned between ethyl acetate and water at pH 6.5. The aqueous phase was separated and freeze-dried to give an amorphous white solid (0.05 g, 56%)

Ir $\nu_{max}$ (Nujol) 3340 (b) 1775, 1720, 1680 cm$^{-1}$ Pmr δ(D$_2$O) 7.00–6.86 (3H, m, aryl protons), 5.48 (1H, d, H-6), 5.34 (1H, s, CH), 5.28 (1H, d, H-5), 4.82 (1H, masked by solvent, H-3), 4.05–3.95 (2H, m, CONCH$_2$), 3.75–3.62 (2H, m, CH$_2$CH$_3$,CH$_2$-CH$_2$), 3.54–3.45(2H, m, CH$_2$CH$_2$), 3.39–3.25 (2H, ddd, H-2×2) and 1.18 (3H, t, CH$_2$CH$_3$)ppm.

EXAMPLE 4

Sodium 6,β-[D,L-2-[3-(3,4-diacetoxyphenylcarbonyl)-3-methyl-1-ureido]-2-(3,4-diacetoxyphenyl)]acetamidobisnorpenicillanate

(a) D,L-2-[3-(3,4-diacetoxyphenylcarbonyl)-3-methyl-1-ureido]-2-(3,4-diacetoxy)phenyl acetic acid D,L-Dihydroxyphenylglycine (0.37 g, 2 mmol) was heated under reflux in trimethylsilyldiethylamine (5 ml) for 0.25 hours to give a clear solution. Excess silylating agent and by-products were removed by evaporation in vacuo and the residue dissolved in dry dichloromethane (5 ml). This solution was cooled to 0° C., treated with triethylamine (0.25 ml, 2 mmol) and then with a solution of N-methyl-3,4-diacetoxybenzamide-N-carbonyl chloride (0.62 g, 2 mmol) in dry dichloromethane (10 ml). The mixture was allowed to warm to 21° C., stirred for 2 hours and then evaporated to low bulk. The residue was dissolved in methanol (10 ml) and acidified to pH 1.5 with dilute hydrochloric acid and stirred for 0.5 hours. The solution was evaporated, the residue partitioned between ethyl acetate and water and the organic phase separated, washed with brine, dried (MgSO$_4$) and evaporated to give a foam (0.83 g, 88%).

This material, D,L-2-[3-(3,4-diacetoxyphenylcarbonyl)-3-methyl-1-ureido]-2-(3,4-dihydroxyphenyl)acetic acid, (0.83 g, 1.8 mmol) in dry tetrahydrofuran (10 ml) at 0° C. was treated with pyridine (0.51 ml, 6.3 mmol) and acetic anhydride (0.51 ml, 5.4 mmol). The solution was allowed to warm to 21° C. and was stirred for 1.5 hours. The residue obtained after evaporation was partitioned between ethyl acetate and water at pH 1.5, the organic phase being separated, washed with brine, dried (MgSO$_4$) and evaporated to give a foam. This material was stirred vigorously in water as the pH was adjusted to 7.2 with sodium bicarbonate solution the aqueous phase was washed with ethyl acetate then acidified to pH 2 with dilute hydrochloric acid and extracted with ethyl acetate. The organic phase was separated, washed with brine, dried (MgSO$_4$) and evaporated to give a white foam (0.46 g, 47%) Ir $\nu_{max}$ (DCM) 1775, 1705, 1680–1660 (b), 1205 cm$^{-1}$.

Pmr δ(d$^6$-acetone) 10.0 (1H, d, NH), 9.5 (1H, s, CO$_2$H), 7.6–7.1 (6H, complex, aryl protons), 5.6 (1H, d, CH), 3.1 (3H, s, NCH$_3$) and 2.3 (12H, s, OCOCH$_3$×4) ppm.

(b) Benzyl 6,β-[D,L-2-[3-(3,4-diacetoxyphenylcarbonyl)-3-methyl-1-ureido]-2-(3,4-diacetoxyphenyl)]acetamidobisnorpenicillanate The above acid (0.28 g, 0.5 mmol) from Example 4(a) in dichloromethane (5 ml) was added, at 0° C., to a stirred solution of benzyl 6β-aminobisnorpenicillanate (0.14 g, 0.5 mmol) and dicyclohexylcarbodiimide (0.11 g, 0.5 mmol) in dry dichloromethane (7 ml). The mixture was allowed to warm to 21° and was stirred for 2 hours. Solid material was filtered off and the filtrate washed with dilute hydrochloric acid, dilute sodium bicarbonate solution, brine, then dried (MgSO$_4$) and evaporated to give a semi-solid material (0.4 g) which was columned on silica eluting with 1:1 n-hexane/ethyl acetate to give the product as a colourless glass (0.2 g, 49%).

Ir $\nu_{max}$ (DCM) 1790 (s) 1780, 1710–1690 (b) 1200 cm$^{-1}$. Pmr δ(CDCl$_3$) 10.00 (1H, d, NH), 7.45–7.20 (11H, complex, aryl protons), 6.75 (1H, d, NH), 5.58 (2H, m, H-6, CH), 5.34 (1H, d, H-5), 5.19 (2H, ABq, CH$_2$), 4.98 (1H, m, H-3) 3.41–3.26 (2H, m, H-2×2), 3.22 (3H, s, NCH$_3$) and 2.30 (12H, s, OCOCH$_3$×4) ppm.

(c) Sodium 6,β-[DL-2-[3-(3,4-diacetoxyphenylcarbonyl) -3-methyl-1-ureido]-2-(3,4-diacetoxyphenyl)- ]acetamidobisnorpenicillanate The above ester (0.17, 0.21 mmol) from Example 4(b) dissolved in tetrahydrofuran (5 ml) with 10% palladium on charcoal (0.17 g) was shaken under an atmosphere of hydrogen for 1 hour. The mixture was filtered through 'Celite', evaporated and the residue partitioned between water at pH 6.5 and ethyl acetate. The aqueous phase was separated and freeze-dried to give the title compound as a white solid (0.098 g, 73%).

Ir $\nu_{max}$ (Nujol) 3300, 1775, 1700, 1660, 1600 cm$^{-1}$. Pmr δ(d$^6$ acetone/CD$_3$OD) 7.5–7.1 (6H, m, aryl protons), 5.7–5.1 (4H, m, H-6, H-3, C$\underline{H}$), 3.6–3.3 (2H, m, H-2×2), 3.2 (3H, s, NC$\underline{H}_3$) and 2.3 (12H, s, OCOC$\underline{H}_3$×4) ppm.

EXAMPLE 5

Sodium 6,β-[D,L-2-(3-phenylcarbonyl-3-methyl-1-ureido)-2-(3,4-dihydroxyphenyl)]acetamidobisnorpenicillanate (a) D,L-2-(3-Phenylcarbonyl-3-methyl-1-ureido)-2-(3,4-dihydroxyphenyl) acetic acid N-Methylbenzamide (0.41 g, 3 mmol) with 4-N,N-dimethylaminopyridine (0.1 g, 0.8 mmol) in dry dichloromethane (4 ml) was treated with triethylamine (0.42 ml, 3 mmol) and then trimethylsilyl chloride (0.38 ml, 3 mmol) for 0.5 hours at 21°. The solution was then heated under reflux for 0.5 hours, cooled, evaporated to ca 1 ml and diluted with dry dichloromethane (5 ml). The solution was cooled to 0°, treated with triethylamine (0.42 ml, 3 mmol) and then phosgene (3 ml of 12.5% solution in toluene) and stirred for 0.45 hours at 0°–10°. The mixture was then evaporated to ca 2 ml and diluted with dichloromethane (5 ml).

DL,3,4-Dihydroxyphenylglycine (0.55 g, 3 mmol) was heated under reflux in trimethylsilyldiethylamine (8 ml) for 0.25 hours. Excess silylating agent and by products were removed by evaporation in vacuo and the persilylated residue dissolved in dry dichloromethane (5 ml). This solution was cooled to 0° and treated with the above N-carbonyl chloride preparation. The mixture was allowed to warm to 21° and was stirred for 2 hours when water (15 ml) and acetone (30 ml) were added. The solution was adjusted to pH 1.5 with 5N hydrochloric acid and stirred vigorously for 0.5 hours when the organic solvents were evaporated in vacuo. The residue was basified to pH 8 with dilute sodium bicarbonate solution and washed with ethyl acetate. The separated aqueous phase was layered with ethyl acetate and acidified to pH 1.5 with dilute hydrochloric acid. The organic layer was separated, washed with brine, dried (MgSO$_4$) and evaporated to give a yellow foam (0.7 g, 68%).

Ir $\nu_{max}$ (Nujol) 3700–2500 (b), 1740 (s) 1690 cm$^{-1}$. Pmr δ(CDCl$_3$/d$^6$acetone) 10.0 (1H, d, NH), 8.5 (3H, bs, OH×2, CO$_2\underline{H}$), 7.4 (5H, s, aryl protons), 6.9 (3H, m, 3,4-dihydroxyphenyl protons), 5.5 (1H, d, C$\underline{H}$) and 3.2 (3H, s, N-C$\underline{H}_3$)ppm.

(b) Benzyl 6,β-[D,L-2-(3-phenylcarbonyl-3-methyl-1-ureido)-2-(3,4-dihydroxyphenyl)acetamidobisnorpenicillanate The above acid (0.2 g, 0.58 mmol) from Example 5(a) in dry tetrahydrofuran (5 ml) was cooled to −15° when N-methylmorpholine (0.064 ml, 0.58 mmol) and methylchloroformate (0.045 ml, 0.08 mmol) was added. The mixture was stirred for 0.75 hours at 0°, concentrated to ca 2 ml and diluted with dry dichloromethane (4 ml). This solution was added, at 0° to a stirred solution of benzyl 6β-aminobisnorpenicillanate (0.16 g, 0.58 mmol) in dry dichloromethane (5 ml). Stirring was continued for 1.75 hours during which time the temperature was allowed to rise to ambient. The solution was washed with dilute hydrochloric acid, dilute sodium bicarbonate solution, brine and was then dried (MgSO$_4$) and evaporated to give a foam (0.28 g). This crude product was columned on silica gel eluting with 1:2 n-hexane/ethyl acetate to give the desired ester as a colorless gum (0.12 g, 37%).

Ir $\nu_{max}$ (DCM) 1795, 1750, 1715 (s) 1695 cm$^{-1}$. Pmr δ(CDCl$_3$/CD$_3$OD) 7.4 (5H, s, aryl protons), 7.3 (5H, s, aryl protons), 6.8 (3H, m, 3,4-dihydroxyphenyl), 5.6 (1H, d, H-6), 5.4 (1H, s, C$\underline{H}$), 5.25 (1H, d, H-5), 5.2 (2H, s, CH$_2$), 5.0 (1H, m, H-3), 3.4 (2H, m, H-2×2) and 3.1 (3H, s, NC$\underline{H}_3$) ppm.

(c) Sodium 6,β-βD,L-2-(3-phenylcarbonyl-3-methyl-1-ureido)-2-(3,4-dihydroxyphenyl)]acetamidobisnorpenicillanate The above ester (0.1 g, 0.16 mmol) from Example 5(b) in tetrahydrofuran (5 ml) with 10% palladium on charcoal (0.1 g) was shaken under an atmosphere of hydrogen for 0.5 hours. More catalyst (0.1 g) was added and hydrogenolysis continued for a further 0.75 hours. The mixture was filtered through 'Celite' evaporated and the residue partitioned between ethyl acetate and water at pH 6.7. The aqueous phase was separated and freeze-dried to give the title compound as a white solid (0.06 g, 70%).

Ir $\nu_{max}$ (Nujol) 3600–3100 (b), 1780, 1710 (s) 1690, 1600 cm$^{-1}$, Pmr δ(CD$_3$OD/D$_2$O) 7.5 (5H, s, aryl protons), 6.8 (3H, m, 3,4-dihydroxyphenyl protons), 5.5 (1H, d, H-6), 5.25 (2H, m, H-5, C$\underline{H}$), 4.7 (H-3 masked by solvent). 3.3 (solid) (H-2×2, masked by solvent), and 3.1 (3H, s, NC$\underline{H}_3$) ppm.

EXAMPLE 6

Sodium 6,β-[D-2-[3-(4-chlorophenylcarbonyl)-3-methyl-1-ureido]-2-(3,4-dihydroxyphenyl)acetamidobisnorpenicillanate.

(a) D-2-[3-(4-chlorophenylcarbonyl)-3-methyl-1-ureido]-2-(3,4-dihydroxyphenyl)acetic acid This acid was prepared using a procedure analogous to that described in example 5(a). Thus 4-chloro-N-methylbenzamide (0.51g, 3mmol) gave the title acid as a foam (1.1 g, 96%)

Ir $\nu_{max}$ (Nujol) 3600–3200(b), 1720(s), 1690, 1510, 1100, 1045, 1020cm$^{-1}$, Pmr δ(CDCl$_3$/CD$_3$OD) 9.9(1H,d,NH), 7.4(4H,s, p-chlorophenyl protons), 6.9(3H,m, 3,4-dihydroxyphenyl protons), 5.4(1H,d,CH) and 3.2(3H,s,NCH$_3$)ppm.

(b) Benzyl 6,β-[D,2-[3-(4-chlorophenylcarbonyl)-3-methyl-1-ureido]-2-(3,4-dihydroxyphenyl)]acetamidobisnorpenicillanate.

This ester was prepared from the reaction of D,2-[3-(4-chlorophenylcarbonyl)-3-methyl-1-ureido]-2-(3,4-dihydroxyphenyl)acetic acid (0.38g, 1 mmol) and benzyl 6β-aminobisnorpenicillanate (0.28g, 1 mmol) using a method analogous to that described in example 5(b). The yield was 0.3g, 47%.

Ir $\nu_{max}$(DCM) 3300(b) 1790, 1750, 1690, 1510, 1340, 1095, 1045, 1020cm$^{-1}$, Pmr δ(CDCl$_3$/CD$_3$OD) 7.4(4H,s,p-chlorophenyl protons), 7.2(5H,s,benzyl protons), 6.9(3H,m,3,4-dihydroxyphenyl protons), 5.5(2H,m,H-6,CH), 5.2(1H,d,H-5 superimposed upon 2H,s,CH$_2$), 4.8(1H,m,H-3), 3.3(2H,m,H-2×2) and 3.1 (3H,s,NCH$_3$)ppm (c) Sodium 6,β-[D,2[3-(4-chlorophenylcarbonyl)-3-methyl-1-ureido]-2-(3,4-dihydroxyphenyl)]acetamidobisnorpenicillanate.

The ester (0.1 g, 0.16 mmol) from example 6(b) was deprotected using an analogous procedure to that described in example 5(c) to give the title compound as a white solid (0.03g, 32%)

Ir $ν_{max}$ (Nujol) 3600–3200(b), 1780, 1720 (s), 1700, 1610, 1100, 1060, 1030cm$^{-1}$ δ(CD$_3$OD) 7.53, 7.45(4H,ABq, p-chlorophenyl protons), 6.89–6.70(3H,m, 3,4-dihydroxyphenylprotons), 5.51(1H,d,H-6), 5.35(1H,s,CH), 5.23(1H,d,H-5), 4.72(1H,dd,H-3), 3.40–3.30(2H,m,H-2×2) and 3.18(3H,s,NCH$_3$)ppm.

| Biological Data - Antibacterial In Vitro Activity | |
|---|---|
| Compound of Example 3 | (MIC mg/ml) |
| E. coli ESS | 0.02 |
| E. coli JT4 | 1.0 |
| E. coli JT425 | 0.05 |
| E. coli NCTC 10418 | 0.02 |
| Ps. aeruginosa NCTC 10662 | 1.0 |
| Ps. aeruginosa NCTC 10662 10$^{-2}$ | 0.1 |
| Ps. aeruginosa Dalgleish 10$^{-2}$ | 2.5 |
| S. marcesens US32 | 0.2 |
| K. aerogenes A | 0.05 |
| E. cloacae N1 | 0.5 |
| P. mirabilis C977 | 0.1 |
| P. mirabilis 899 | 100 |
| P. rettgeri | 0.2 |
| S. aureus Oxford | 5.0 |
| S. aureus Russell | 50 |
| N. catarrhalis 1502 | 0.02 |
| S. faecalis I | 50 |
| S. pyogenes CN10 | 0.5 |

I claim:
1. A compound of the formula (I):

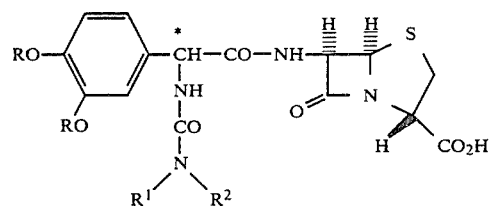

or a pharmaceutically acceptable salt or in-vivo hydrolyzable ester thereof wherein R is hydrogen, alkylcarbonyl of 1 to 6 carbon atoms in the alkyl moiety or alkyl of 1 to 6 carbon atoms; R$^1$ is hydrogen or a hydrocarbon; R$^2$ is hydrogen, or an optionally substituted hydrocarbon or optionally substituted heterocyclyl or CXR$^d$, wherein X is O or S and R$^d$ is hydrogen or an optionally substituted hydrocarbon or optionally substituted heterocyclyl; or R$^1$ and R$^2$ together with the nitrogen to which they are attached, for an optionally substituted heterocyclyl group.

2. A compound according to claim 1 wherein R is hydrogen or acetyl.

3. A compound according to claim 1 wherein R$^1$ is hydrogen or alkyl or 1 to 6 carbon atoms.

4. A compound according to claim 3 wherein R$^2$ is a group COR$^d$ wherein R$^d$ is hydrogen or optionally substituted hydrocarbon or optionally substituted heterocyclyl.

5. A compound according to claim 1 of the formula (II):

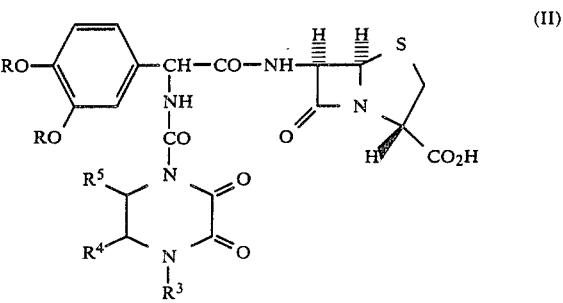

or a phamaceutically acceptable salt or in-vivo hydrolysable ester thereof wherein R is hydrogen, alkylcarbonyl of 1 to 6 carbon atoms in the alkyl moiety or alkyl of 1 to 6 carbon atoms; R$^3$ is hydrogen or alkyl of 1 to 6 carbon atoms; R$^4$ and R$^5$ are the same or different and each is hydrogen, alkyl of 1 to 6 carbon atoms, halogen, amino, hydroxy or alkoxy of 1 to 6 carbon atoms.

6. 6β[D-2-(4-Ethyl-2,3-dioxopiperazine-1-carbonylamino)-2-(2,4-dihydroxyphenyl)]acetamidobisnorpenicillanic acid;

6,β-[D,L-2(4-ethyl-2,3-dioxopiperazine-1-carbonylamino)-2-(3,4-dihdroxyphenyl)]acetamidobisnorpenicillanic acid;

6, β[D,L-2[3-(3,4-diacetoxyphenylcarbonyl)-3-methyl-1-ureido]-2-(3,4-diacetoxyphenyl)]acetamidobisnorpenicillanic acid;

6, β-[D,L-2(3-phenylcarbonyl-3-methyl-1-ureido)-2-(3,4-dihydroxyphenyl)]acetamidobisnorpenicillanic acid;

6, β-[D-2[3-(4-chlorophenylcarbonyl)-3-methyl-1-ureido]-2-(3,4-dihydroxyphenyl)]acetamidobisnorpenicillanic acid or pharmaceutically acceptable salt or in vivo hydrolysable ester thereof.

7. A pharmaceutical composition useful for treating bacterial infections in humans and animals which comprises and antibacterially effective amount of a compound of the formula (I):

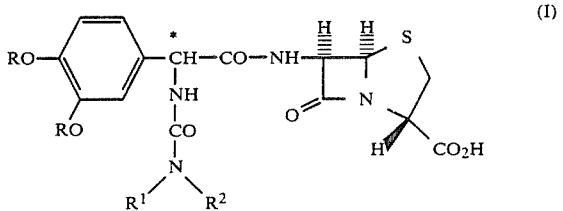

or a pharmaceutically acceptable salt or in-vivo hydrolysable ester thereof wherein R is hydrogen, alkylcarbonyl of 1 to 6 carbon atoms in the alkyl moiety or alkyl of 1 to 6 carbon atoms; R$^1$ is hydrogen or a hydrocarbon; R$^2$ is hydrogen, or an optionally substituted hydrocarbon or optionally substituted heterocyclyl or CXR$^d$, wherein X is O or S and R$^d$ is hydrogen or an optionally substituted hydrocarbon or optionally substituted heterocyclyl; or R$^1$ and R$^2$ together with the nitrogen to which they are attached, form an optionally substituted heterocyclyl group, in combination with a pharmaceutically acceptable carrier.

8. A composition according to claim 7 wherein R is hydrogen or acetyl.

9. A composition according to claim 7 wherein $R^1$ is hydrogen or alkyl of 1 to 6 carbon atoms.

10. A composition according to claim 7 wherein $R^2$ is a group $COR^d$ wherein $R^d$ is hydrogen or optionally substituted hydrocarbon or optionally substituted heterocyclyl.

11. A composition according to claim 7 wherein the compound is of the formula (II):

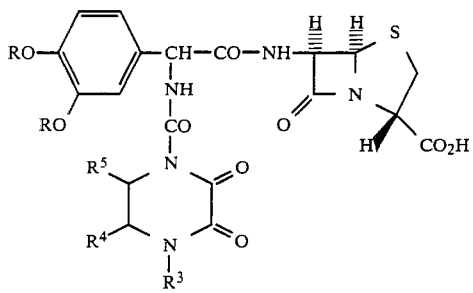

or a pharmaceutically acceptable salt or pharmaceutically acceptable in-vivo hydrolyzable ester thereof wherein R is hydrogen, alkylcarbonyl of 1 to 6 carbon atoms in the alkyl moiety or alkyl of 1 to 6 carbon atoms; $R^3$ is hydrogen or alkyl of 1 to 6 carbon atoms; $R^4$ and $R^5$ are the same or different and each is hydrogen, alkyl of 1 to 6 carbon atoms, halogen, amino, hydroxy or alkoxy of 1 to 6 carbon atoms.

12. A composition according to claim 7 wherein the compound is:

6β[D-2-(4-Ethyl-2,3-dioxopiperazine-1carbonylamino-2-(3,4-dihydroxyphenyl)]acetamidobisnorpenicillanic acid;

6,β-[D,L-2-(4-ethyl-2,3-dioxopiperazine-1-carbonylamino)-2-(3,4-dihydroxyphenyl)]acetamidobisnorpenicillanic acid;

6,β-[D,L-2-[3-(3,4-diacetoxyphenylcarbonyl)-3-methyl-1-ureido]-2-(3,4-diacetoxyphenyl)]acetamidobisnorpenicillanic acid;

6,β-[D,L-2-(3-phenylcarbonyl-3-methyl-1-ureido)-2-(3,4-dihydroxyphenyl)]acetamidobisnorpenicillanic acid;

6,β-2-[D-2-[3-(4-chlorophenylcarbonyl)-3-methyl-1-ureido]-2-(3,4-dihydroxylphenyl)]acetamidobisnorpenicillanic acid or a pharmaceutically acceptable salt or in-vivo hydrolysable ester thereof.

13. A method of treating bacterial infections in humans and animals which comprises administering to a human or animal in need thereof an antibacterially effective amount of a compound of the formula (I):

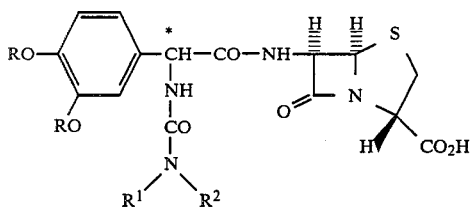

or a pharmaceutically acceptable salt or in-vivo hydrolyzable ester thereof wherein R is hydrogen, alkylcarbonyl of 1 to 6 carbon atoms in the alkyl moiety or alkyl of 1 to 6 carbon atoms; $R^1$ is hydrogen or a hydrocarbon; $R^2$ is hydrogen, or an optionally substituted hydrocarbon or optionally substituted heterocyclyl or $CXR^d$, wherein X is O or S and $R^d$ is hydrogen or an optionally substituted hydrocarbon or optionally substituted heterocyclyl; or $R^1$ and $R^2$ together with the nitrogen to which they are attached, form an optionally substituted heterocyclyl group, in combination with a pharmaceutically acceptable carrier.

14. A method according to claim 13 wherein R is hydrogen or acetyl.

15. A method according to claim 13 wherein $R^1$ is hydrogen or alkyl of 1 to 6 carbon atoms.

16. A method according to claim 13 wherein $R^2$ is a group $COR^d$ wherein $R^d$ is hydrogen or optionally substituted hydrocarbon or optionally substituted heterocyclyl.

17. A method according to claim 13 wherein the compound is of the formula (II):

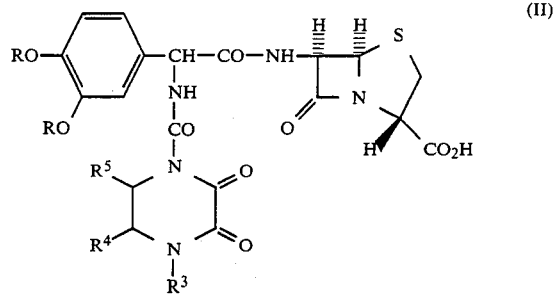

or a pharmaceutically acceptable salt or pharmaceutically acceptable in-vivo hydrolyzable ester thereof wherein R is hydrogen, alkylcarbonyl of 1 to 6 carbon atoms in the alkyl moiety or alkyl of 1 to 6 carbon atoms; $R^3$ is hydrogen or alkyl of 1 to 6 carbon atoms; $R^4$ and $R^5$ are the same or different and each is hydrogen, alkyl of 1 to 6 carbon atoms, halogen, amino, hydroxy or alkoxy of 1 to 6 carbon atoms.

18. A method according to claim 13 wherein the compound is:

6β[D-2-(4-Ethyl-2,3-dioxopiperazine-1-carbonylamino)-2-(3,4-dihydroxyphenyl)]acetamidobisnorpenicillanic acid;

6,β-[D,L-2-(4-ethyl-2,3-dioxopiperazine-1-carbonylamino)-2-(3,4-dihydroxyphenyl)]acetamidobisnorpenicillanic acid;

6,β-[D,L-2-[3-(3,4-diacetoxyphenylcarbonyl)-3-methyl-1-ureido]-2-(3,4-diacetoxyphyenyl)]acetamidobisnorpenicillanic acid;

6-β-[D,L-2-(3-phenylcarbonyl-3methyl-1-ureido)-2-3,4-dihydroxyphenyl)]acetamidobisnorpenicillanic acid, 6,βD-2-[3-(4-chlorophenylcarbonyl)-3-methyl-1ureido]-2-(3,4-dihydroxylphenyl)]acetamidobisnorpenicillanic acid or a pharmaceutically acceptable salt or in-vivo hydrolysable ester thereof.

19. A pharmaceutical composition useful for treating bacterial infections in humans and animals which comprises a β-lactamase inhibitory amount of a β-lactamase inhibitor and an antibacterially effective amount of a compound of the formula (I):

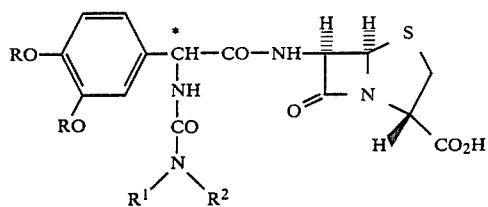

or a pharmaceutically acceptable salt or pharamaceutically acceptable in-vivo hydrolyzable ester thereof wherein R is hydrogen, alkylcarbonyl of 1 to 6 carbon atoms in the alkyl moiety or alkyl of 1 to 6 carbon atoms; $R^1$ is hydrogen or a hydrocarbon; $R^2$ is hydrogen, or an optionally substituted hydrocarbon or optionally substituted heterocyclyl or $CXR^d$, wherein X is O or S and $R^d$ is hydrogen or an optionally substituted hydrocarbon or optionally substituted heterocyclyl; or $R^1$ and $R^2$ together with the nitrogen to which they are attached, form an optionally substituted heterocyclyl group, in combination with a pharmaceutically acceptable carrier.

20. A composition according to claim 19 wherein R is hydrogen or acetyl.

21. A composition according to claim 19 wherein $R^1$ is hydrogen or alkyl of 1 to 6 carbon atoms.

22. A composition according to claim 19 wherein $R^2$ is a group $COR^d$ wherein $R^d$ is hydrogen or optionally substituted hydrocarbon or optionally substituted heterocyclyl.

23. A composition according to claim 19 wherein the compound is of the formula (II):

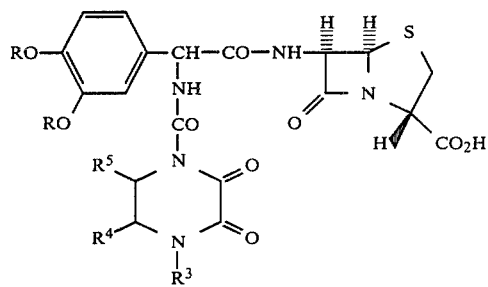

or a pharmaceutically acceptable salt or pharamaceutically acceptable in-vivo hydrolyzable ester thereof wherein R is hydrogen, alkylcarbonyl of 1 to 6 carbon atoms in the alkyl moiety or alkyl of 1 to 6 carbon atoms; $R^3$ is hydrogen or alkyl of 1 to 6 carbon atoms; $R^4$ and $R^5$ are the same or different and each is hydrogen, alkyl of 1 to 6 carbon atoms, halogen, amino, hydroxy or alkoxy of 1 to 6 carbon atoms.

24. A composition according to claim 19 wherein the compound is:

6β[D-2-(4-Ethyl-2,3-dioxopiperazine-1-carbonylamino)-2-(3,4-dihydroxyphenyl)]acetamidobisnorpenicillanic acid;

6,β-[D,L-2-(4-ethyl-2,3-dioxopiperazine-1-carbonylamino)-2-(3,4-dihydroxyphenyl)]acetamidobisnorpenicillanic acid;

6,β[-D,L-2-[3-(3,4-diacetoxyphenylcarbonyl)-3-methyl-1-ureido]-2-(3,4-diacetoxyphenyl)]acetamidobisnorpenicillanic acid;

6,β[D,L-2-(3-phenylcarbonyl-3-methyl-1-ureido)-2-(3,4-dihydroxyphenyl)]acetamidobisnorpenicillanic acid;

6,β-[D-2-[3-(4-chlorophenylcarbonyl)-3-methyl-1-ureido]-2-(3,4-dihydroxylphenyl)]acetamidobisnorpenicillanic acid or a pharmaceutically acceptable salt or in-vivo hydrolysable ester thereof.

25. A method of treating bacterial infections in humans and animals which comprises administering to a human or animal in need thereof a β-lactamase inhibitory amount of a β-lactamase inhibitor and an antibacterially effective amount of a compound of the formula (I):

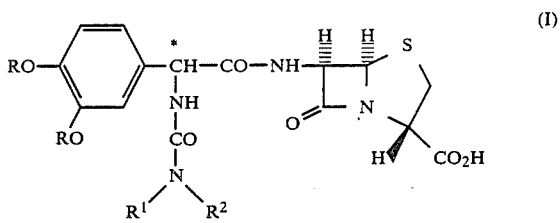

or a pharmaceutically acceptable salt or pharmaceutically acceptable in-vivo hydrolyzable ester thereof wherein R is hydrogen, alkylcarbonyl of 1 to 6 carbon atoms in the alkyl moiety or alkyl of 1 to 6 carbon atoms; $R^1$ is hydrogen or a hydrocarbon; $R^2$ is hydrogen, or an optionally substituted hydrocarbon or optionally substituted heterocyclyl or $CXR^d$, wherein X is O or S and $R^d$ is hydrogen or an optionally substituted hydrocarbon or optionally substituted heterocyclyl; or $R^1$ and $R^2$ together with the nitrogen to which they are attached, form an optionally substituted heterocyclyl group, in combination with a pharmaceutically acceptable carrier.

26. A method according to claim 20 wherein R is hydrogen or acetyl.

27. A method according to claim 25 wherein $R^1$ is hydrogen or alkyl of 1 to 6 carbon atoms.

28. A method according to claim 25 wherein $R^2$ is a group $COR^d$ wherein $R^d$ is hydrogen or optionally substituted hydrocarbon or optionally substituted heterocyclyl.

29. A method according to claim 25 wherein the compound is of the formula (II):

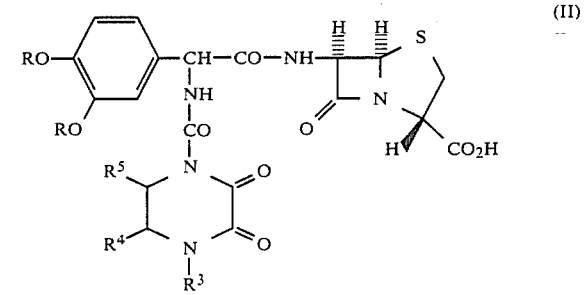

or a pharamaceutically acceptable salt or pharmaceutically acceptable in-vivo hydrolyzable ester thereof wherein R is hydrogen, alkylcarbonyl of 1 to 6 carbon atoms in the alkyl moiety or alkyl of 1 to 6 carbon atoms; $R^3$ is hydrogen or alkyl of 1 to 6 carbon atoms; $R^4$ and $R^5$ are the same or different and each is hydrogen, alkyl of 1 to 6 carbon atoms, halogen, amino, hydroxy or alkoxy of 1 to 6 carbon atoms.

30. A method according to claim 25 wherein the compound is:

6β[D-2-(4-Ethyl-2,3-dioxopiperazine-1-carbonylamino-2-(3,4-dihydroxyphenyl)]acetamidobisnorpenicillanic acid;

6,β-[D,L-2-(4-ethyl-2,3-dioxopiperazine-1-carbonylamino)-2-(3,4-dihydroxyphenyl)]acetamidobisnorpenicillanic acid;

6,β[D,L-2-[3-(3,4-diacetoxyphenylcarbonyl)-3-methyl-1-ureido]-2-(3,4-diacetoxyphenyl)]acetamidobisnorpenicillanic acid;

6,β-[D,L-2-(3-methyl-1-ureido)-3-(3,4-dihydroxyphenyl)]acetamidobisnorpenicillanic acid;

6,β-[D-2-[3-(4-chlorophenylcarbonyl)-3-methyl-1-ureido]-2 2-(3,4-dihydroxylphenyl)]acetamidobisnorpenicillanic acid or a pharmaceutically acceptable salt or in-vivo hydrolysable ester thereof.

* * * * *